United States Patent
Dejima et al.

(10) Patent No.: US 10,736,613 B2
(45) Date of Patent: *Aug. 11, 2020

(54) TISSUE SAMPLING DEVICE

(71) Applicant: FUJIFILM Corporation, Tokyo (JP)

(72) Inventors: Takumi Dejima, Kanagawa (JP);
Shinichi Yamakawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/800,703

(22) Filed: Jul. 16, 2015

(65) Prior Publication Data

US 2015/0313580 A1    Nov. 5, 2015

Related U.S. Application Data

(63) Continuation of application No. PCT/JP2014/050556, filed on Jan. 15, 2014.

(30) Foreign Application Priority Data

Jan. 21, 2013  (JP) .................................. 2013-008715

(51) Int. Cl.
   *A61B 10/02*   (2006.01)
   *A61B 10/04*   (2006.01)
   *A61B 8/12*    (2006.01)

(52) U.S. Cl.
   CPC ............ *A61B 10/0266* (2013.01); *A61B 8/12* (2013.01); *A61B 10/0233* (2013.01); *A61B 10/04* (2013.01); *A61B 10/0241* (2013.01); *A61B 2010/045* (2013.01)

(58) Field of Classification Search
   None
   See application file for complete search history.

(56) References Cited

U.S. PATENT DOCUMENTS

| | | | |
|---|---|---|---|
| 5,928,162 A | 7/1999 | Giurtino et al. | |
| 6,015,381 A | * 1/2000 | Ouchi ..................... | A61B 10/06 600/104 |
| 6,063,037 A | 5/2000 | Mittermeier et al. | |
| 6,086,543 A | 7/2000 | Anderson et al. | |
| 6,569,151 B1 | 5/2003 | Nash et al. | |
| 6,755,793 B2 | 6/2004 | Lamoureux et al. | |

(Continued)

FOREIGN PATENT DOCUMENTS

| | | |
|---|---|---|
| IE | S77150 | 11/1997 |
| JP | 52-040615 | 9/1977 |

(Continued)

OTHER PUBLICATIONS

Toshikazu, JP 2000232983 A—Machine Translation, Aug. 29, 2000.*

(Continued)

*Primary Examiner* — Sean P Dougherty
*Assistant Examiner* — Benjamin S Melhus
(74) *Attorney, Agent, or Firm* — JCIPRNET

(57) ABSTRACT

A tissue sampling device including a flexible sheath, a cannula inserted into the sheath so as to be movable back and forth and punctured into body tissue, and an operation unit provided on a proximal end side of the sheath to move the cannula back and forth, wherein the cannula has a distal end part including a slit extending from a distal end opening toward a proximal end side.

7 Claims, 14 Drawing Sheets

(56) References Cited

U.S. PATENT DOCUMENTS

| | | | |
|---|---|---|---|
| 6,872,192 | B2 | 3/2005 | Nash et al. |
| 2006/0235334 | A1 | 10/2006 | Corvi et al. |
| 2007/0055215 | A1* | 3/2007 | Tran .................. A61B 10/0275 604/540 |
| 2007/0185416 | A1 | 8/2007 | Melsheimer |
| 2007/0213634 | A1 | 9/2007 | Teague |
| 2008/0132930 | A1 | 6/2008 | Lubock et al. |
| 2008/0234699 | A1* | 9/2008 | Oostman, Jr. ...... A61B 10/0266 606/133 |
| 2009/0287114 | A1 | 11/2009 | Lee et al. |
| 2012/0197157 | A1 | 8/2012 | Ryan et al. |
| 2012/0245487 | A1* | 9/2012 | Eells .................. A61B 10/0275 600/567 |
| 2013/0158429 | A1 | 6/2013 | Lee-Sepsick et al. |
| 2015/0073299 | A1 | 3/2015 | Vetter et al. |
| 2016/0081678 | A1 | 3/2016 | Kappel et al. |

FOREIGN PATENT DOCUMENTS

| | | | |
|---|---|---|---|
| JP | S62261355 | | 11/1987 |
| JP | 03-019847 | | 4/1991 |
| JP | 10-192286 | | 7/1998 |
| JP | 2000232983 | A * | 8/2000 |
| JP | 2002095749 | | 4/2002 |
| JP | 2005-073798 | | 3/2005 |
| JP | 3661470 | | 6/2005 |
| WO | 2011136719 | | 11/2011 |
| WO | 2011139876 | | 11/2011 |

OTHER PUBLICATIONS

"Written Opinion of the International Searching Authority of PCT/JP2014/050556", this report contains the following items: Form PCT/ISA237(cover sheet), PCT/ISA237(Box No. I), PCT/ISA237(Box No. V), dated Mar. 18, 2014, which is English translation of "Written Opinion of the International Searching Authority", pp. 1-9.

"Office Action of Japan Counterpart Application" with English translation, dated Jun. 7, 2016, p. 1-p. 6.

"The Extended European Search Report of European Counterpart Application", dated Jan. 28, 2016, pp. 1-7.

"The Extended European Search Report of European Counterpart Application", dated May 2, 2016, pp. 1-7.

"Office Action of Japan Counterpart Application" with English translation thereof, dated Aug. 19, 2016, p. 1-p. 6.

"PCT/IB/373:International Preliminary Report on Patentability" dated Dec. 1, 2015, including "PCT/ISA/237:Written Opinion of the International Searching Authority of PCT/JP2014/063654", which is English translation of "PCT/ISA237:Written Opinion of the International Searching Authority", pp. 1-11.

"Office Action of U.S. Co-pending U.S. Appl. No. 14/951,499", dated Nov. 1, 2017, p. 1-p. 31, in which the listed references were cited.

"Office Action of U.S. co-pending Application, U.S. Appl. No. 14/951,499", dated Jun. 8, 2018, p. 1-p. 16.

"Office Action of U.S. Related U.S. Appl. No. 14/951,499", dated Mar. 15, 2019, pp. 1-17.

"Office Action of U.S. Appl. No. 14l/951,499", dated Jun. 12, 2020, pp. 1-10.

* cited by examiner

FIG.5
(a)
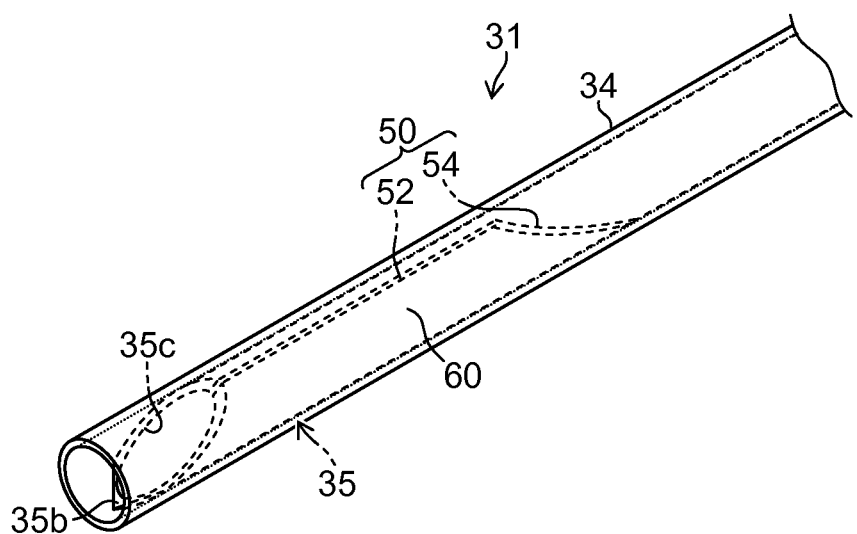
(b)
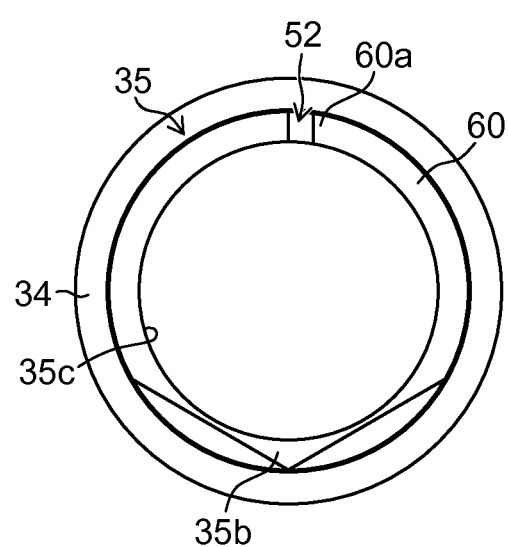
(c)
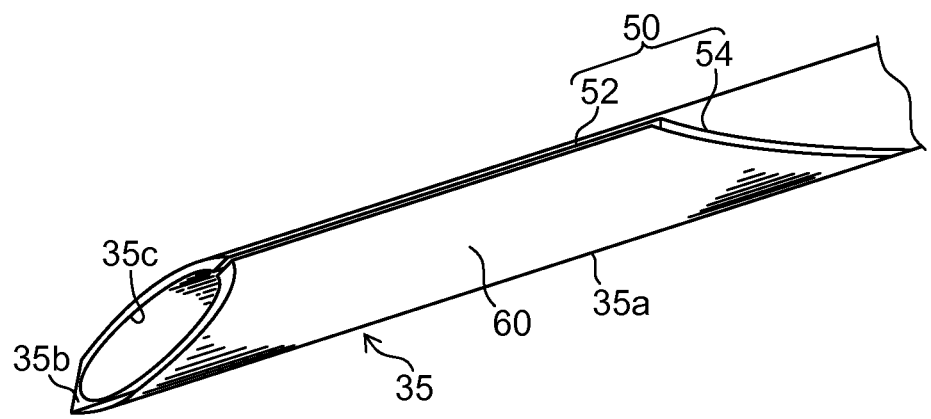

FIG.6
(a)
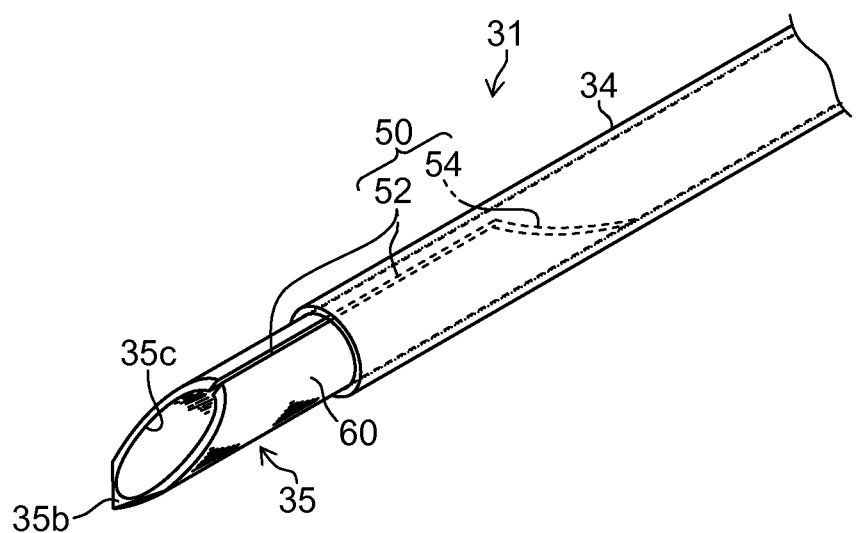
(b)
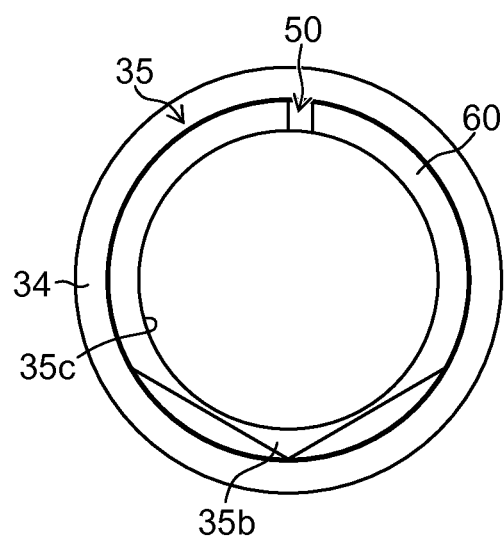

FIG.7
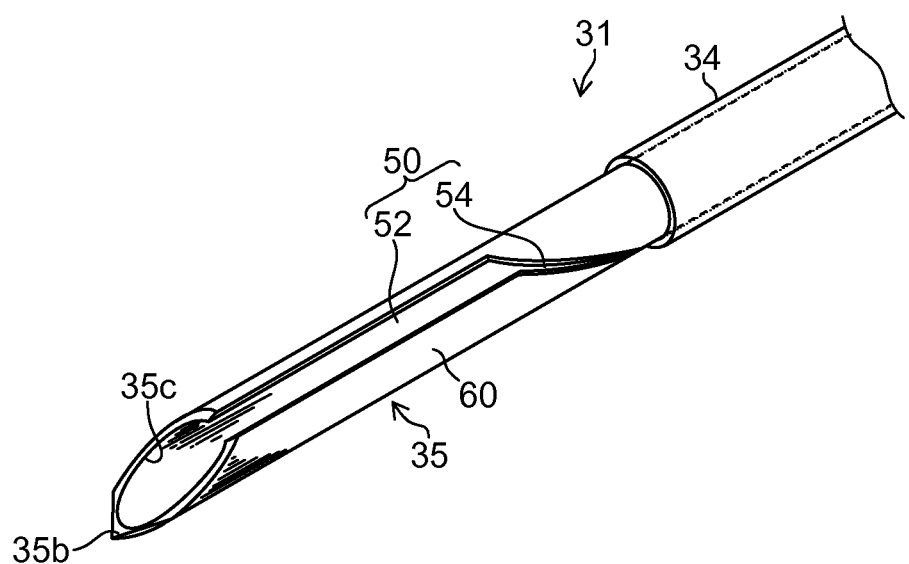
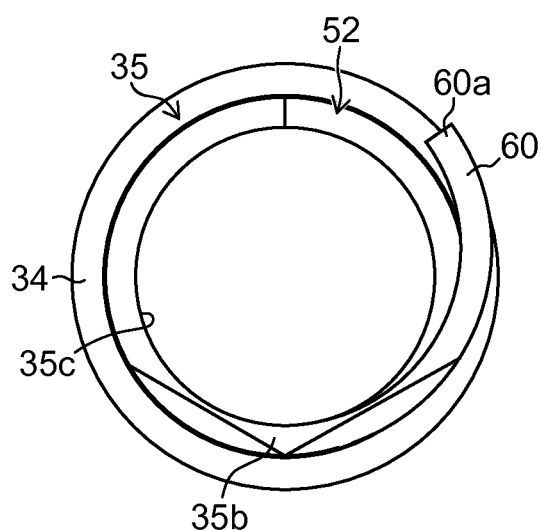
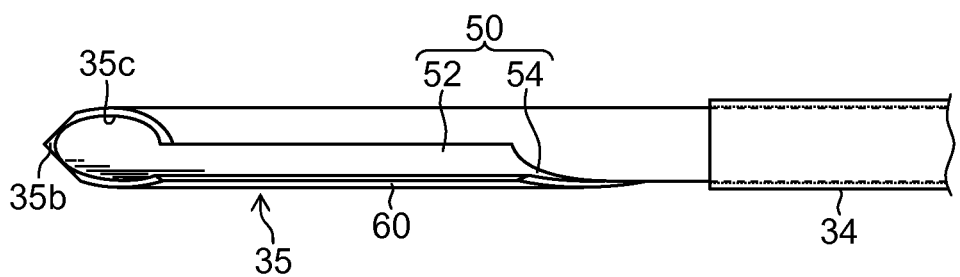

FIG.8
(a)
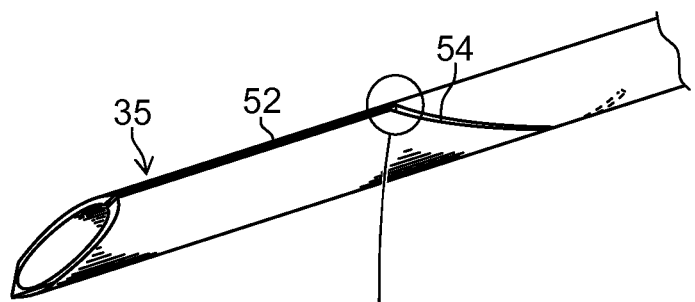
(b)
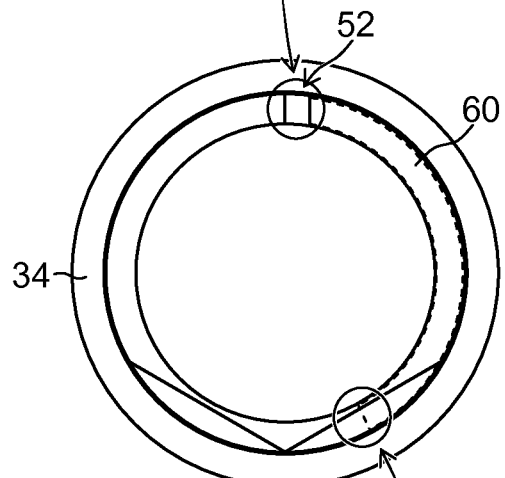
(c)
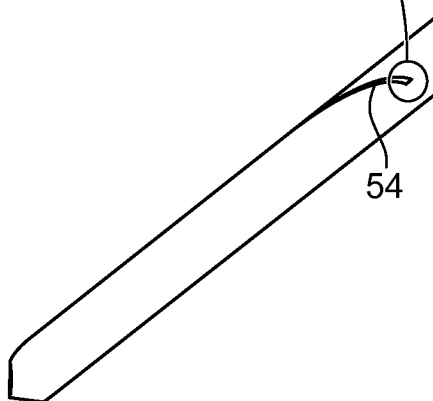

FIG.9
(a)
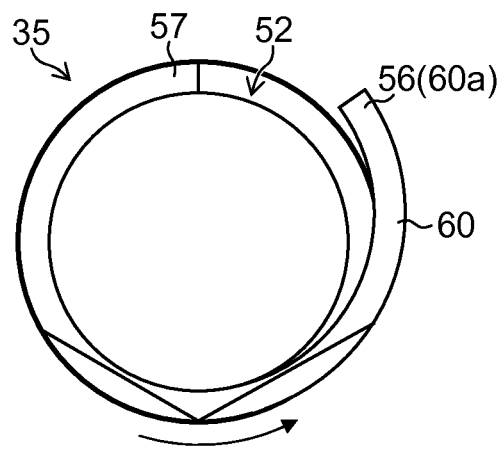
(b)
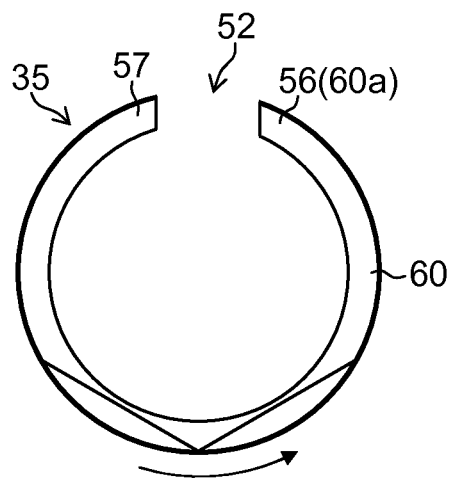

FIG.13
(a)
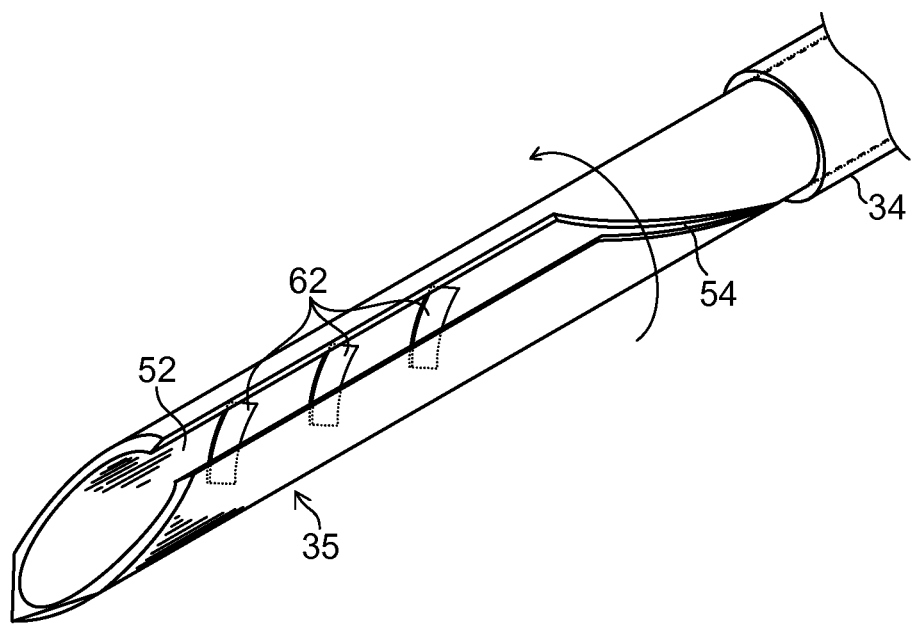
(b)
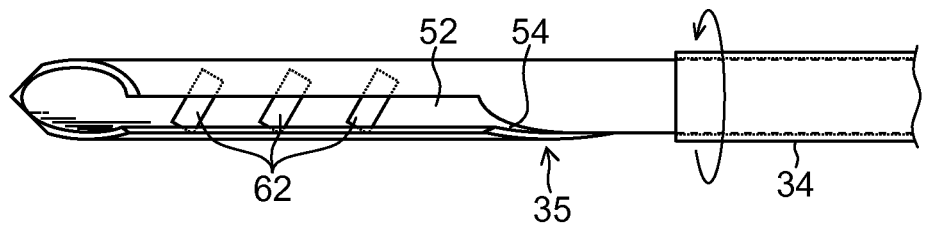

TISSUE SAMPLING DEVICE

CROSS-REFERENCE TO RELATED APPLICATIONS

This application is a Continuation of PCT International Application No. PCT/JP2014/050556 filed on Jan. 15, 2014, which claims priority under 35 U.S.C§119(a) to Japanese Patent Application No. 2013-8715 filed on Jan. 21, 2013. Each of the above application(s) is hereby expressly incorporated by reference, in its entirety, into the present application.

BACKGROUND OF THE INVENTION

Field of the Invention

The present invention relates to a tissue sampling device, and more particularly to a tissue sampling device for use in sampling body tissue.

Description of the Related Art

In recent years, a pathological definitive diagnosis has been made in such a manner that a puncture needle is introduced into a body cavity through a treatment tool insertion channel of an ultrasonic endoscope so that a cannula constituting the puncture needle is guided up to a region to be observed and is punctured into a diseased tissue to sample body tissue under ultrasonic tomographic image observation by the ultrasonic endoscope.

For example, there has been known a tissue sampling device for use in making such a pathological definitive diagnosis as disclosed in Japanese Patent Application Laid-Open No. 2005-73798 (hereinafter referred to as PTL 1). The tissue sampling device comprises a sheath flexible enough to be freely inserted into the treatment tool insertion channel of the endoscope; a cannula (puncture needle) inserted into the sheath so as to be movable back and forth and punctured into body tissue; and an operation unit connected to a proximal end portion of the sheath to move the cannula back and forth.

SUMMARY OF THE INVENTION

The pathological definitive diagnosis is generally divided into two types: cytological diagnosis and tissue diagnosis. The cytological diagnosis is intended to diagnose cells by checking one by one. Thus, it is difficult to determine whether or not a specimen is benign or malignant and it is difficult to obtain information leading to a pathological definitive diagnosis. Meanwhile, the tissue diagnosis is a method of diagnosing body tissue by checking a whole mass of body tissue, and thus information enough to make a pathological definitive diagnosis can be easily obtained. Therefore, it is desirable to sample a sufficient amount of body tissue enough to make the tissue diagnosis when the pathological definitive diagnosis is made.

However, the prior art tissue sampling device as disclosed in PTL 1 has a difficulty in sampling a sufficient amount of body tissue because the cannula introduced into the body cavity through the treatment tool insertion channel of the endoscope has a thin shape with a diameter, for example, less than 1 mm and has a structure in which a sharp cutting edge formed at a distal end of the cannula is inserted into body tissue thereby to trap the body tissue inside from a distal end opening of the cannula, the structure of which allows a very small amount of body tissue to be sampled. Therefore, an insufficient amount of sampled body tissue requires the cannula to be punctured a plurality of times, and hence requires complicated operation.

In order to solve this problem, it is considered to increase an outer diameter of the cannula constituting the puncture needle to increase the amount of sampled body tissue. However, it is difficult to increase the amount of sampled tissue because the increase in diameter of the cannula is limited by the limit in diameter of the treatment tool insertion channel of the endoscope. In addition, an increase in diameter of the cannula requires an increase in rigidity of the cannula, and hence it is difficult to perform an operation for introducing the cannula to a region to be observed in the body cavity through the treatment tool insertion channel of the endoscope.

In view of such circumstances, the present invention has been made, and an object of the present invention is to provide a tissue sampling device capable of easily sampling a sufficient amount of body tissue enough to make a pathological definitive diagnosis.

In order to achieve the above object, an aspect of the present invention provides a tissue sampling device comprising: a flexible sheath; a cannula inserted into the sheath so as to be movable back and forth and punctured into body tissue; and an operation unit provided on a proximal end side of the sheath to move the cannula back and forth, wherein the cannula has a distal end part including a slit extending from a distal end opening toward a proximal end side.

In an aspect of the tissue sampling device according to the present invention, the cannula is configured such that a curvature radius of a first edge part of edge parts provided on both sides of the slit is larger than the curvature radius of a second edge part thereof.

In an aspect of the tissue sampling device according to the present invention, in a state where the distal end part of the cannula is protruded from the distal end of the sheath, the first edge part enlarges its diameter radially outward more than an inner surface of the sheath when viewed from an axial direction of the cannula.

In an aspect of the tissue sampling device according to the present invention, the proximal end side of the slit is spirally formed in the axial direction of the cannula.

In an aspect of the tissue sampling device according to the present invention, the distal end part of the cannula is less than or equal to an inner diameter of the sheath when housed in the sheath.

In an aspect of the tissue sampling device according to the present invention, the slit extends to the proximal end side from other than a sharpened tip portion of the distal end opening of the cannula.

In an aspect of the tissue sampling device according to the present invention, the slit extends to the proximal end side from the sharpened tip portion of the distal end opening of the cannula.

In an aspect of the tissue sampling device according to the present invention, the operation unit includes a rotary operation unit rotating the cannula.

In an aspect of the tissue sampling device according to the present invention, at least one edge part of the edge parts provided on both sides of the slit is formed in a sharp edge shape.

In an aspect of the tissue sampling device according to the present invention, at least one edge part of the edge parts provided on both sides of the slit is formed in a sawtooth shape.

In an aspect of the tissue sampling device according to the present invention, the inner surface of the distal end part of the cannula includes a guide member for guiding body tissue trapped inside the distal end part of the cannula to the proximal end side when the cannula is rotated.

The present invention provides a slit at the distal end part of the cannula. The slit extends from the distal end opening to the proximal end side. Thus, rotation of the cannula punctured into the body tissue allows a larger amount of body tissue to be sampled through a gap formed by the slit. Therefore, a sufficient amount of body tissue enough to make a pathological definitive diagnosis can be easily sampled.

BRIEF DESCRIPTION OF THE DRAWINGS

FIG. 5 is a schematic configuration view illustrating a configuration of the distal end portion of the cannula constituting the tissue sampling device in a state in which the distal end portion of the cannula is housed in a sheath.

FIG. 6 is a schematic configuration view illustrating the configuration of the distal end portion of the cannula constituting the tissue sampling device in a state in which a part of the distal end portion of the cannula is projected from the distal end of the sheath.

FIG. 7 is a schematic configuration view illustrating the configuration of the distal end portion of the cannula constituting the tissue sampling device in a state in which the entire distal end portion of the cannula is projected from the distal end of the sheath.

FIG. 8 is an explanatory drawing illustrating a positional relationship between the distal end opening of the cannula, a sharpened tip portion thereof, and a proximal end side slit thereof FIG. 9 is an explanatory drawing for describing a curvature radius of the cannula.

FIG. 13 is a perspective view and a plan view illustrating a distal end part of the cannula according to a third modification.

DETAILED DESCRIPTION OF THE PREFERRED EMBODIMENTS

Hereinafter, a preferable embodiment of the present invention will be described in detail with reference to the accompanying drawings.

The description will now focus on a configuration in which a tissue sampling device for puncture to which the present invention is applied is inserted into a body cavity through a treatment tool insertion channel formed in an ultrasonic endoscope for performing electronic convex scanning, but as a guide means of the tissue sampling device, an ultrasonic endoscope using a scanning system other than the electronic convex scanning and a treatment tool insertion channel of a normal endoscope without an ultrasonic diagnosis mechanism may be used. Alternatively, a trocar or the like may be used as the guide means. When the tissue sampling device is inserted into a trocar, the whole may also be made of a rigid member.

Figure 1:
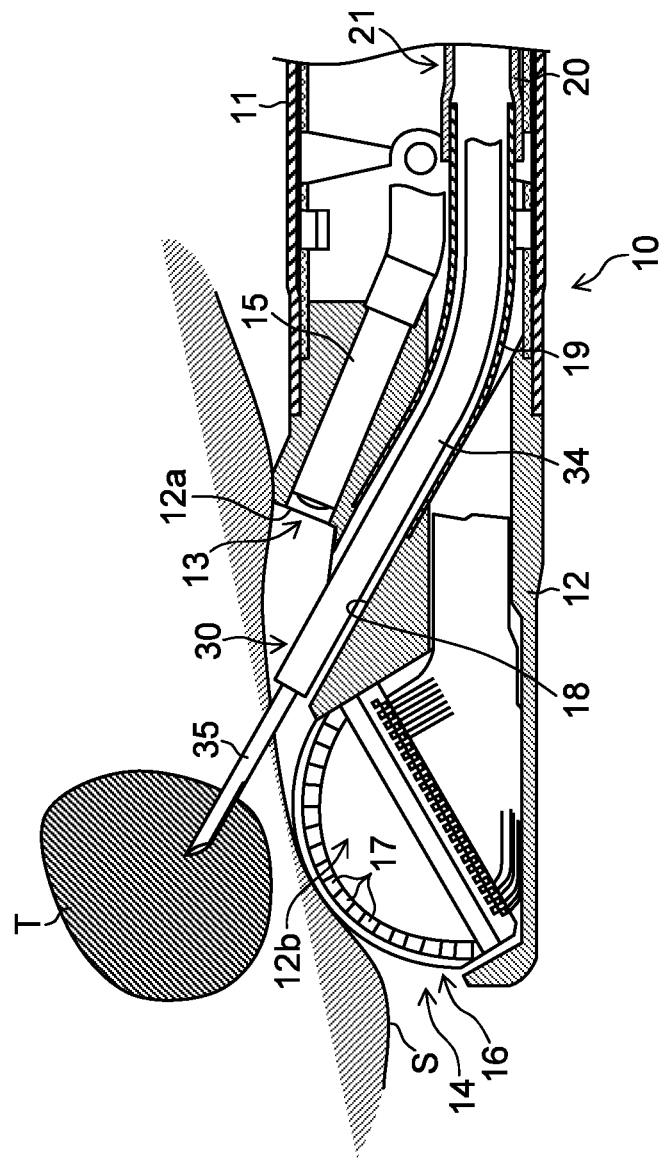
FIG. 1 is a sectional view of an essential part illustrating a state in which a tissue sampling device according to an embodiment of the present invention is incorporated into an ultrasonic endoscope.

First, FIG. 1 illustrates a configuration of a distal end portion of an ultrasonic endoscope that guides the tissue sampling device. In the Figure, reference numeral 10 designates an insertion unit into a body cavity. The insertion unit 10 includes a distal end body 12 continuously connected to a distal end of an angle portion 11. The distal end body 12 includes an endoscopic observation unit 13 on a proximal end side thereof and an ultrasonic observation unit 14 at a distal end side thereof. The endoscopic observation unit 13 is disposed at an inclined portion 12a on the proximal end side of the distal end body 12 and orients its observation field obliquely forward.

FIG. 1 illustrates an illumination mechanism 15 having a light guide constituting the endoscopic observation unit 13. An observation mechanism is provided together with the illumination mechanism 15, but the observation mechanism is not illustrated herein. Note that a solid-state imaging element or an image guide is used as the observation mechanism.

The ultrasonic observation unit 14 includes an ultrasonic transducer unit 16 mounted in an opening portion 12b disposed at the distal end of the distal end body 12. The ultrasonic transducer unit 16 is intended to perform electronic convex scanning and includes a large number of strip-shaped ultrasonic transducers 17 arranged in an arc shape.

A treatment tool deriving port 18 is formed between the endoscopic observation unit 13 and the ultrasonic observation unit 14. The treatment tool deriving port 18 is a passage drilled at the distal end body 12 with a predetermined inner diameter. The treatment tool deriving port 18 is connected to a connection pipe 19. The connection pipe 19 is bent at a predetermined angle and its proximal end portion is connected to a flexible tube 20. Thus, the treatment tool insertion channel 21 includes the treatment tool deriving port 18, the connection pipe 19, and the flexible tube 20. The treatment tool deriving port 18 extends obliquely forward relative to the axis of the insertion unit 10. The flexible tube 20 extends in the axial direction of the insertion unit 10. The connection pipe 19 has an intermediate portion bent at a predetermined angle.

Reference numeral 30 designates the tissue sampling device. The tissue sampling device 30 is inserted into the treatment tool insertion channel 21 and can advance and retract into and from the treatment tool deriving port 18. In a state in which the distal end body 12 abuts against an intracavitary wall S, a body tissue sampling point T is set in the ultrasonic observation field by the ultrasonic observation unit 14, and the distal end of the tissue sampling device 30 is inserted into the intracavitary wall S from the treatment tool deriving port 18 until the distal end reaches the tissue sampling point T, where the body tissue can be sampled.

Figure 2:
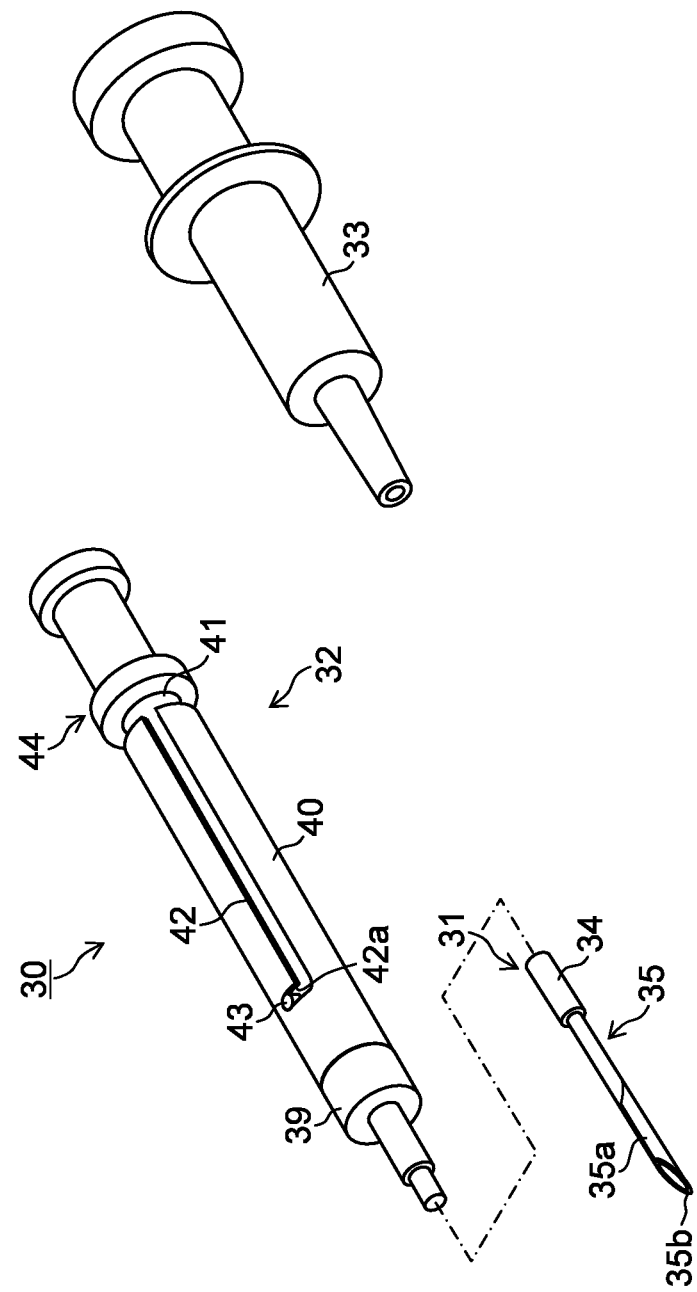
FIG. 2 is an entire configuration view of the tissue sampling device.

FIG. 2 is an entire configuration view of the tissue sampling device 30. As is apparent from the Figure, the tissue sampling device 30 includes an insertion unit 31 and an operation unit 32. The proximal end portion of the operation unit 32 is detachably connected to a syringe 33.

Figure 3:
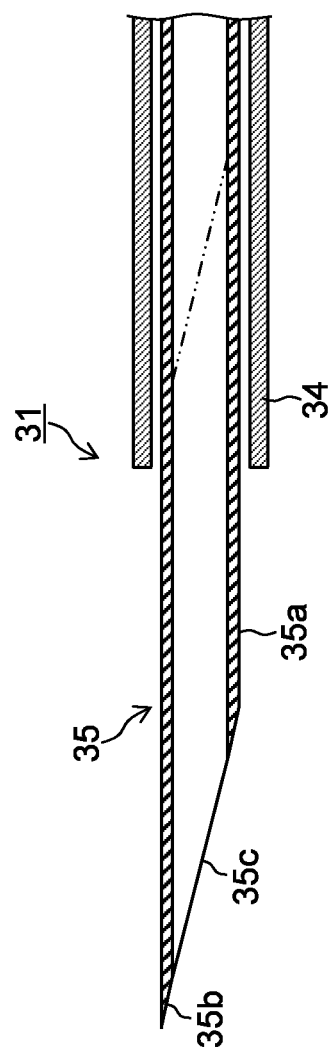
FIG. 3 is a sectional view of a distal end portion of an insertion unit constituting the tissue sampling device.
Figure 4:
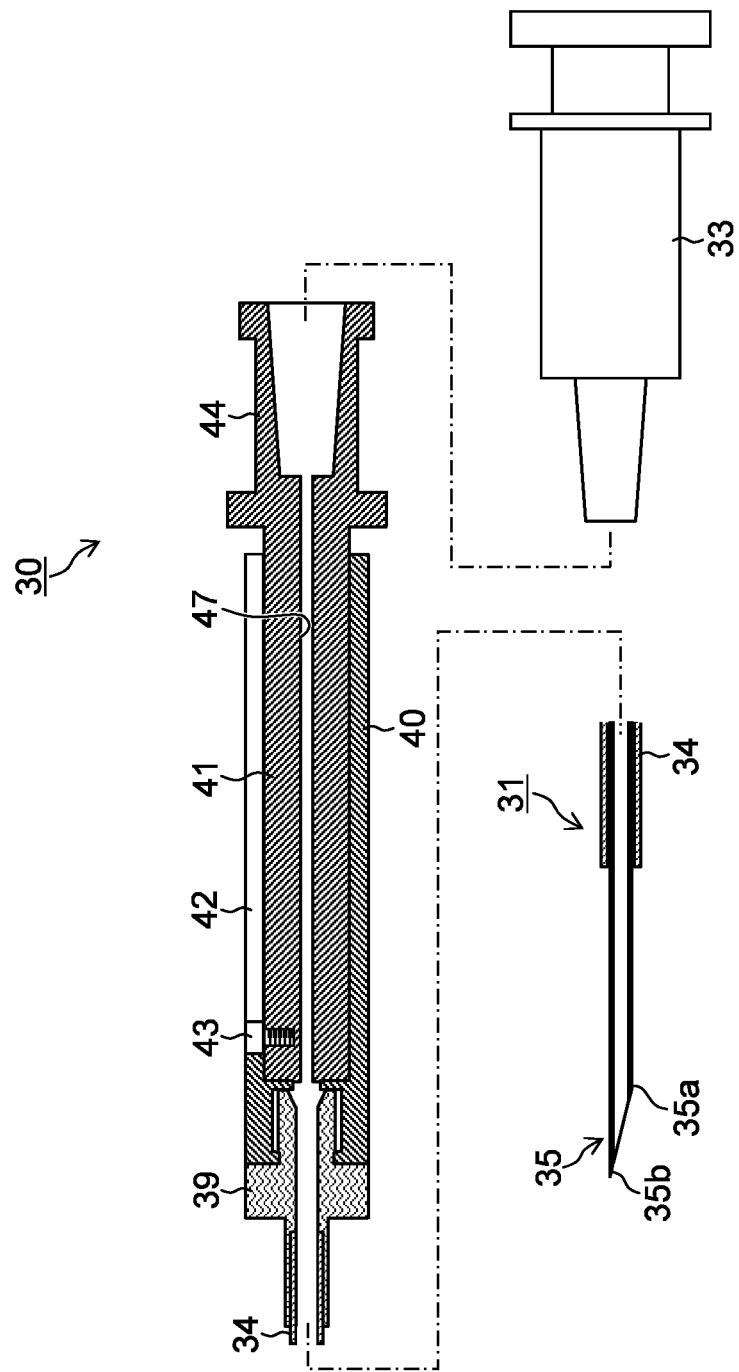
FIG. 4 is a sectional view of the tissue sampling device.

The insertion unit 31 is longer than at least the total length of the treatment tool insertion channel 21 and is made of a double cylindrical member as illustrated in FIG. 3. More specifically, the insertion unit 31 includes a sheath 34 on an outermost side thereof and a cannula 35 inserted into the sheath 34.

The sheath 34 is intended to be inserted into the treatment tool insertion channel of the endoscope and makes up an exterior of the insertion unit 31. The sheath 34 is made of a flexible cylindrical member such as a resin member such as polyether sulfone or Teflon (registered trademark). Alternatively, the sheath 34 may be made of a contact coil or the like.

The cannula 35 is intended to be punctured into body tissue to sample diseased tissue or the like and is disposed and inserted into the sheath 34 so as to be movable back and forth therein. The cannula 35 includes a thin-walled-pipe-like body pipe 35a with its distal end being open and a needle tip 35b serving as a sharpened tip portion formed by cutting away the distal end portion of the body pipe 35a at an angle. Note that since the cannula 35 is punctured into the body, the distal end part thereof including at least the needle tip 35b must be rigid and hence is made of a rigid member.

Here, in order to allow the insertion unit 31 to be inserted into the treatment tool insertion channel 21, the insertion unit 31 must be flexible in a bending direction enough to smoothly pass through the bent connection pipe 19 even in a state in which the angle portion 11 is bent. In light of this, the portion other than the distal end part including the needle tip 35b of the cannula 35 may be made of a flexible tube and the insertion unit 31 may be configured to include the tube connected to a rigid pipe. Meanwhile, the cannula 35 is small in diameter and thin enough to be bent. Thus, the entire cannula 35 is made of a pipe member such as metal or the like.

The cannula 35 is configured to be movable in a back and forth direction inside the sheath 34 such that the needle tip 35b moves between a retracted position (position illustrated in phantom in FIG. 3) covered with the sheath 34 and an actuated position (position illustrated by a solid line in FIG. 3) at which the needle tip 35b is projected by a predetermined length from the distal end of the sheath 34.

Then, the proximal end portion of the sheath 34 is connected to the operation unit 32 so that an operation of the operation unit 32 causes the cannula 35 to advance and retract into and from the distal end of the sheath 34. A specific configuration of the operation unit 32 is illustrated in FIG. 2.

The proximal end portion of the sheath 34 is disposed and fixed to a coupling member 39. The coupling member 39 is coupled to a casing 40. The casing 40 is made of a cylindrical member having a predetermined length, into which a slider 41 is slidably inserted in the axial direction of the casing 40. The slider 41 is hollow and the proximal end portion of the cannula 35 is fixed into the slider 41. Therefore, a push and pull operation of the slider 41 causes the needle tip 35b at the distal end of the cannula 35 to advance and retract into and from the distal end of the sheath 34.

A guide hole 42 having a predetermined length in the axial direction is provided on a surrounding body of the casing 40. The slider 41 includes a pin 43 to be inserted into the guide hole 42. The distal end of the guide hole 42 is bent at an angle of about 90° so as to form a positioning hole portion 42a oriented in the circumferential direction. The rear end of the guide hole 42 extends up to the rear end of the casing 40.

The retracted position of the cannula 35 is in a state in which the slider 41 is pulled out of the casing 40 and the cannula 35 is pulled into the sheath 34. When the pin 43 is pulled out of the rear end of the guide hole 42, for example, to enter a state of abutting against the rear end of the casing 40 (portion in which the guide hole 42 is not provided), the cannula 35 can be held in the retracted position. In the retracted position, the needle tip 35b of the cannula 35 is placed slightly inside the distal end of the sheath 34 and the needle tip 35b is completely covered with the sheath 34. Thus, the cannula 35 can be smoothly inserted into the treatment tool insertion channel 21 while ensuring safety without allowing the needle tip 35b to puncture or hook other objects when the cannula 35 is inserted into the treatment tool insertion channel 21 or the like. Note that in the state in which the slider 41 is pulled out of the casing 40 from the state in which the pin 43 abuts against the rear end of the casing 40, that is, in the state in which the pin 43 is not engaged with the guide hole 42, the cannula 35 is completely covered with the sheath 34. Thus, the position of the cannula 35 in that state is also in the retracted position.

Meanwhile, when the pin 43 is engaged with the guide hole 42 and the slider 41 is pushed into the casing 40, the cannula 35 is pulled out of the sheath 34. Then, when the pin 43 is disposed at a position engaged with the positioning hole portion 42a at the distal end of the guide hole 42, the cannula 35 is projected by a predetermined length from the sheath 34. This is a puncturable actuated position, and the projection length at this actuated position is the maximum insertion length into the body.

As used herein, the maximum insertion length of the cannula 35 refers to a length by which the cannula 35 can be inserted up to the position at which the sheath 34 abuts against the intracavitary wall. Even in this state, the needle tip 35b needs to be placed within the ultrasonic observation field by the ultrasonic transducer unit 16. Thus, the maximum insertion length of the cannula 35 is restricted by the ultrasonic observation field.

In order to move the pin 43 disposed on the slider 41 side from the guide hole 42 of the casing 40 to the positioning hole portion 42a in the aforementioned actuated position and stabilize the pin 43 at the position, the casing 40 and the slider 41 may be relatively rotated. Further, when the width of transition portion from the guide hole 42 to the positioning hole portion 42a is made slightly narrower than the outer diameter of the pin 43, a click feeling can be obtained at transition and the pin 43 can be stably held.

In order to stabilize the slider 41 in the aforementioned retracted position, the pin 43 may be moved to a position retracted from the axial line of the guide hole 42 by relatively rotating the casing 40 and the slider 41 so that the pin 43 removed from the guide hole 42 may not be easily engaged with guide hole 42. Further, when the width near the rear end of the guide hole 42 is made slightly narrower than the outer diameter of the pin 43, a click feeling can be obtained when the slider 41 moves to the retracted position and the slider 41 can be stably held in the retracted position without the need to retract the pin 43 from the axial line of the guide hole 42.

The cannula 35 is intended to function as a fluid passage. The fluid passage acts as a suction passage for generating a negative pressure and a passage for pumping a liquid such as a formalin solution for use in discharging the tissue trapped inside the cannula 35. The slider 41 includes a flow channel 47 as an extension portion of the fluid passage in the cannula 35. The proximal end portion of the slider 41 is a luer lock portion 44 detachably coupled to a syringe 33 for suction and liquid pumping.

Now, the configuration of the distal end portion of the insertion unit 31 as a feature of the present invention will be described in detail.

FIGS. 5 to 7 are a schematic configuration view illustrating the configuration of the distal end portion of the insertion unit 31. FIG. 5 illustrates a state in which the distal end part of the cannula 35 is housed in the sheath 34. (a) portion is an external perspective view. (b) portion is a front view viewed from the distal end side. (c) portion is a perspective view of only the cannula 35 extracted from the insertion unit 31. FIG. 6 illustrates a state in which the distal end part of the cannula 35 is partially projected from the distal end of the sheath 34. (a) portion is an external perspective view. (b) portion is a front view viewed from the distal end side. FIG. 7 illustrates a state in which the distal end part of the cannula 35 is completely projected from the distal end of the sheath 34. (a) portion is an external perspective view. (b) portion is a front view viewed from the distal end side. (c) portion is a plan view viewed from above.

As illustrated in FIGS. 5 to 7, the distal end part of the cannula 35 is configured to be expandable and retractable so as to advance and retract from and into the distal end of the sheath 34. Specifically, an elastic piece 60 elastically deformable in the radial direction is provided so as to advance and retract from and into the distal end of the sheath 34. The elastic piece 60 is a cantilevered portion formed by a slit 50 (52, 54) to be described later. The elastic piece 60 is subjected to deformation processing (forming processing) by heat treatment or the like so that the free end portion 60a is positioned radially outward from the inner surface of the sheath 34 when viewed from the axial direction of the cannula 35 (see (b) portion in FIG. 7).

As illustrated in FIGS. 5 and 6, in the state in which at least part of the distal end part of the cannula 35 is housed in the sheath 34, the elastic piece 60 is biased radially inward by the sheath 34 and the distal end part of the cannula 35 enters a reduced diameter state. Meanwhile, as illustrated in FIG. 7, in the state in which the distal end part of the cannula 35 is projected from the distal end of the sheath 34, the elastic piece 60 is free from the restriction by the sheath 34, and hence the distal end part of the cannula 35 enters a radially outward enlarged diameter state.

In order to form such an elastic piece 60, the slit 50 is disposed in a side portion of the distal end part of the cannula 35. The slit 50 includes a distal end side slit 52 and a proximal end side slit 54.

The distal end side slit 52 is an elongated through-hole formed linearly along the axial direction toward the proximal end side from the distal end opening 35c of the cannula 35. The distal end side slit 52 is not particularly limited to its shape as long as the free end portion 60a of the cantilevered elastic piece 60 can be formed. For example, the distal end side slit 52 may be formed along a direction inclined obliquely at a predetermined angle relative to the axial direction and may be any of various shapes such as sawtooth and wave shapes.

The distal end side slit 52 is disposed at a position different in phase from the needle tip 35b of the cannula 35. More specifically, the distal end side slit 52 and the needle tip 35b are disposed at positions that do not overlap with each other when the respective portions are projected on a projection surface perpendicular to the axial direction of the cannula 35. This configuration can suppress an increase in insertion resistance (puncture resistance) received from the body tissue when the cannula 35 is punctured into the body tissue, thus improving the operability.

The proximal end side slit 54 is an elongated through-hole extending helically in the axial direction toward the proximal end side from the end portion on the proximal end side of the distal end side slit 52. Like the distal end side slit 52, the proximal end side slit 54 is not particularly limited to its shape as long as the free end portion of the cantilevered elastic piece 60 can be formed, but it is preferable that the proximal end side slit 54 is formed helically along the axial direction in the same manner as in the present embodiment. In this configuration, when the distal end part of the cannula 35 is housed in the sheath 34, the biasing force that the elastic piece 60 receives radially inward from the sheath 34 is gradually increased in proportion to the length to be accommodated in the sheath 34, and hence the distal end part of the cannula 35 can be housed in the sheath 34 in a smooth and easy manner. Therefore, the body tissue trapped inside the distal end part of the cannula 35 can be held in the sheath 34 in a reliably grabbed state. For this reason, the insertion unit 31 can be pulled out of the treatment tool insertion channel 21 without the sampled body tissue falling off on the way.

The proximal end side slit 54 is disposed at a position different in phase from the needle tip 35b of the cannula 35 in the same manner as the distal end side slit 52. More specifically, as illustrated in FIG. 8, when the respective portions are projected on the projection surface perpendicular to the axial direction of the cannula 35, the proximal end side slit 54 is formed in a state in which the phase is shifted so that the needle tip 35b of the cannula 35 is not included in a circumferential range in which the proximal end side slit 54 is formed. According to this configuration, even if the elastic piece 60 is expanded radially outward when the distal end part of the cannula 35 is projected from the distal end of the sheath 34, the needle tip 35b is not directly affected by the deformation of the elastic piece 60, and hence the position of the needle tip 35b is always fixed, thereby allowing stable puncture.

In the present embodiment, the outer diameter of the distal end part of the cannula 35 projected from the distal end of the sheath 34 has two different curvatures. Specifically, as illustrated in (a) portion of FIG. 9, first and second edge parts 56 and 57 provided on respective sides of the distal end side slit 52 are configured such that the first edge part 56 (a free end portion 60a of the elastic piece 60) on a side where the elastic piece 60 is provided has a larger curvature radius than the curvature radius of the second edge part 57. For this reason, as illustrated in (b) portion of FIG. 9, unlike the configuration where the edge parts 56 and 57 have the same curvature radius, a step is formed between the edge parts 56 and 57. Thus, when the cannula 35 is rotated in the counterclockwise direction in the Figure (that is, from a small curvature radius side to a large curvature radius side), a larger amount of body tissue can be sampled through a gap formed by the step.

Note that in the present embodiment, (a) portion of FIG. 9 illustrates a more preferable configuration where the edge parts 56 and 57 have a different curvature radius from each other, but not only the configuration of the present embodiment but also a configuration where the edge parts 56 and 57 have the same curvature radius as illustrated in (b) portion of FIG. 9 can also sample a sufficiently larger amount of body tissue through the distal end side slit 52 than a prior art configuration (that is, a structure trapping body tissue inside from the distal end opening of the cannula). The same is true for modifications to be described later.

The present embodiment is configured as described above. The description will now move on to a method of sampling body tissue using the tissue sampling device 30.

First, the distal end body 12 of the ultrasonic endoscope is located at a predetermined position relative to the intracavitary wall S. In this state, when a tissue sampling point in the body is captured in the observation field of the ultrasonic transducer unit 16 constituting the ultrasonic observation unit 14, the insertion unit 31 is inserted into the treatment tool insertion channel 21 and its distal end part is positioned near the distal end of the treatment tool deriving port 18. Note that the syringe 33 is connected to the luer lock portion 44, and the syringe 33 for suction is used.

Here, the distal end part of the cannula 35 in the insertion unit 31 in a state before being inserted into the intracavitary wall S is covered with the sheath 34. In this state, the slider 41 in the operation unit 32 is operated to be pushed into the casing 40, thereby to project the distal end part of the cannula 35 from the distal end of the sheath 34 as illustrated in (a) portion of FIG. 10. Then, the distal end part of the cannula 35 enters an enlarged diameter state to increase the intracavitary volume of the distal end part. Then, in the enlarged diameter state of the distal end part of the cannula 35, the needle tip 35b in the distal end part is punctured into the body from the intracavitary wall S.

The puncture path of the cannula 35 into the body can be captured in the ultrasonic observation field. Thus, the puncture operation can be safely performed and the tissue sampling point T can be reliably aimed at.

Figure 10:
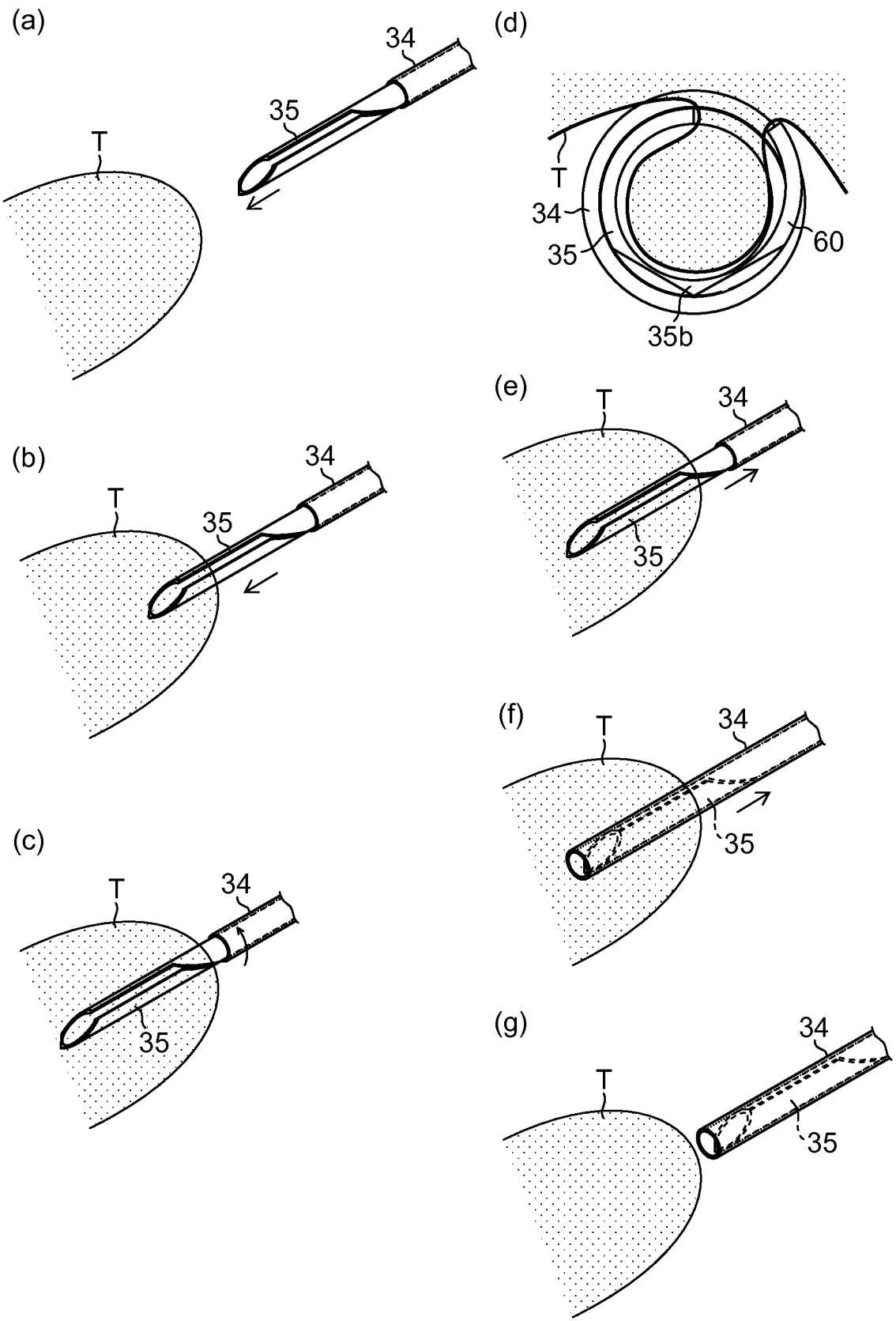
FIG. 10 is an explanatory drawing illustrating a method of sampling body tissue using the tissue sampling device.

As illustrated in (b) portion of FIG. 10, when the needle tip 35b of the cannula 35 advances and penetrates up to the body tissue sampling point T, the syringe 33 is operated to generate a negative pressure inside the cannula 35. The action of the negative pressure causes the body tissue to be transferred through the distal end opening 35c of the cannula 35 into the cannula 35, and thus the body tissue is sampled into the cannula 35. Note that the operation of sampling the body tissue into the cannula 35 is not limited to this. For example, the body tissue may be sampled simply by puncturing the cannula 35 into the body tissue without generating a negative pressure inside the cannula 35. Alternatively, in the state in which the needle tip 35b of the cannula 35 penetrates up to the body tissue sampling point T, the body tissue may be reliably sampled into the cannula 35 by operating the syringe 33 to repeatedly switch between the negative pressure and the positive pressure inside the cannula 35 and at the same time to change the direction of the needle tip 35b of the cannula 35, or the like.

After the needle tip 35b of the cannula 35 is punctured into the body tissue sampling point T, the operation unit 32 is operated to rotate the cannula 35 as illustrated in (c) portion of FIG. 10. Here, the outer diameter of the distal end part of the cannula 35 has two different curvatures, and a step is formed between the two edge parts of the distal end side slit 52. Thus, when the cannula 35 is rotated, a larger amount of body tissue can be trapped into the distal end part of the cannula 35 through a gap formed by the step as illustrated in (d) portion of FIG. 10.

As described above, the body tissue is sampled into the insertion unit 31 of the tissue sampling device 30, and then the insertion unit 31 is pulled out of the treatment tool insertion channel 21. At this time, as illustrated in (e) portion of FIG. 10, in the state in which the distal end part of the cannula 35 is projected from the distal end of the sheath 34, the insertion unit 31 is pulled out of the treatment tool insertion channel 21.

Note that the operation of pulling out the insertion unit 31 from the treatment tool insertion channel 21 is not limited to this. For example, the sheath 34 advances toward the body tissue sampling point T and the distal end part of the cannula 35 is housed in the sheath 34 as illustrated in (f) portion of FIG. 10, and then the insertion unit 31 may be pulled out of the treatment tool insertion channel 21 as illustrated in (g) portion of FIG. 10. In this case, the insertion unit 31 can be pulled out of the treatment tool insertion channel 21 in the state of reliably grabbing the body tissue sampled into the distal end part of the cannula 35 housed in the sheath 34.

The insertion unit 31 is pulled out of the treatment tool insertion channel 21, and then instead of the syringe for suction, for example, a syringe for pumping a formalin solution is connected to the luer lock portion 44, and then the formalin solution is pumped out from the syringe into the cannula 35. This allows the sampled tissue to be transferred into a test tube or the like.

As described above, according to the present embodiment, the distal end part of the cannula 35 is configured to be expandable and retractable so as to advance and retract from and into the distal end of the sheath 34, and thus a sufficient amount of body tissue enough to make a pathological definitive diagnosis can be easily sampled. In addition, the outer diameter of the distal end part of the cannula 35 in the state of projecting from the distal end of the sheath 34 has two different curvatures, and a step is formed between the edge parts 56 and 57 of the distal end side slit 52. Thus, a larger amount of body tissue can be sampled through a gap formed by the step by rotating the cannula 35 punctured into the body tissue.

Hereinbefore, the tissue sampling device according to the present invention has been described in detail, but the present invention is not limited to the above embodiment, and it will be apparent that various improvements and modifications can be made to the present invention without departing from the spirit and scope of the present invention. Hereinafter, some modifications will be described.

[First Modification]

Figure 11:
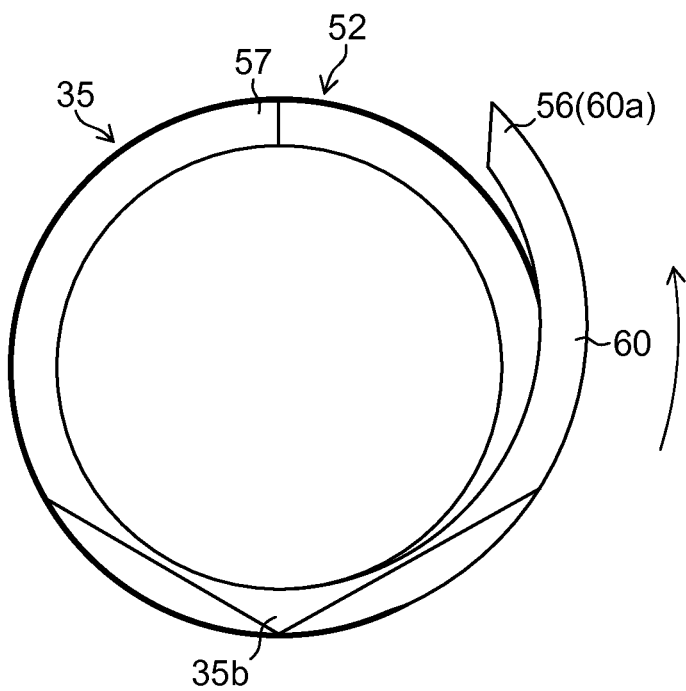
FIG. 11 is a front view illustrating a distal end part of the cannula according to a first modification.

In the first modification illustrated in FIG. 11, of the two edge parts 56 and 57 of the distal end side slit 52 formed in the distal end part of the cannula 35, the first edge part 56 (the free end portion 60a of the elastic piece 60) is configured in a sharp blade shape (tapered edge shape). According to this configuration, the body tissue trapped inside the cannula 35 can be easily cut off by rotating the cannula 35 in the counterclockwise direction in the Figure.

Note that the first modification can increase the amount of sampled body tissue without rotating the cannula 35.

Note that not only the first edge part 56 but also the second edge part 57 may be configured in a sharp blade shape. For example, in a configuration where the edge parts 56 and 57 have the same curvature radius, the body tissue can be efficiently sampled without being influenced by the rotation of the cannula 35.

[Second Modification]

Figure 12:
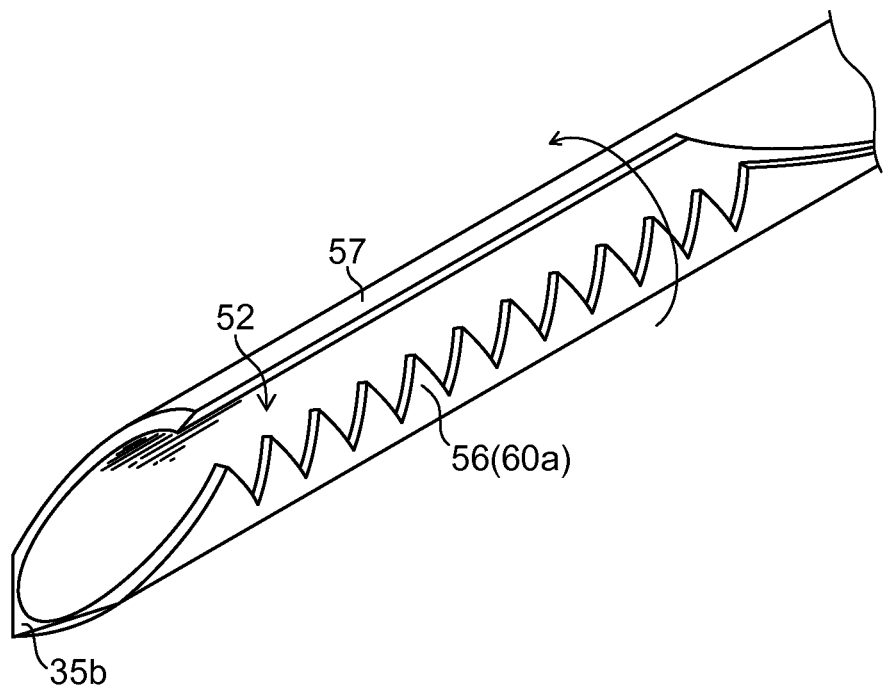
FIG. 12 is a perspective view illustrating a distal end part of the cannula according to a second modification.

In the second modification illustrated in FIG. 12, of the two edge parts 56 and 57 of the distal end side slit 52 formed in the distal end part of the cannula 35, the first edge part 56 (the free end portion 60a of the elastic piece 60) is configured in a sawtooth shape. According to this configuration, like the first modification, the body tissue trapped inside the cannula 35 can be easily cut off by rotating the cannula 35 in the direction indicated by the arrow in the Figure.

Note that the second modification can increase the amount of sampled body tissue without rotating the cannula 35.

Note that not only the first edge part 56 but also the second edge part 57 may be configured in a sawtooth shape. For example, in a configuration where the edge parts 56 and 57 have the same curvature radius, the body tissue can be efficiently sampled without being influenced by the rotation of the cannula 35.

[Third Modification]

In the third modification illustrated in FIG. 13, one or a plurality of guide members 62 are provided in an inner surface of the distal end part of the cannula 35. The guide members 62 are protrudingly disposed in a state of being inclined obliquely relative to the axial direction. When the cannula 35 is rotated in the direction indicated by the arrow in the Figure, the body tissue trapped inside the cannula 35 is guided to the proximal end side of the cannula 35, thereby allowing a larger amount of body tissue to be sampled.

[Fourth Modification]

Figure 14:
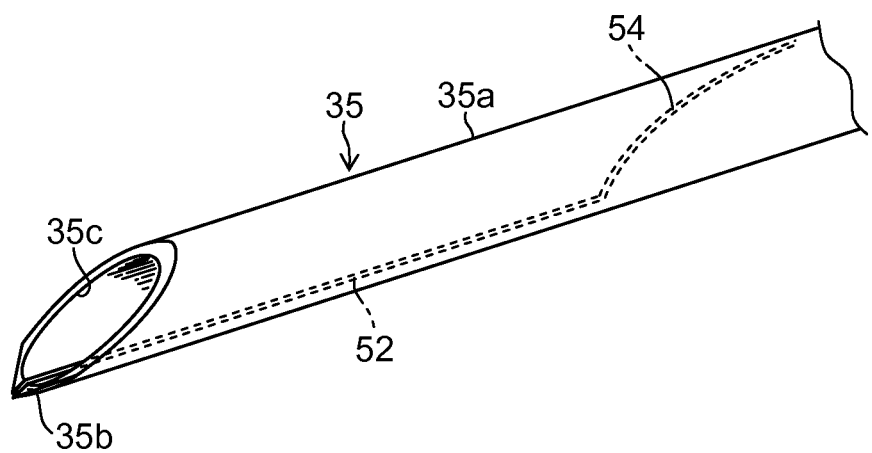
FIG. 14 is a perspective view illustrating a distal end part of the cannula according to a fourth modification.

In the fourth modification illustrated in FIG. 14, the distal end side slit 52 and the proximal end side slit 54 are formed by varying the phase by 180 degrees from that of the present embodiment. More specifically, the distal end part of the cannula 35 includes the linear distal end side slit 52 formed along the axial direction from the needle tip 35b as a sharpened tip portion located at the most advanced end of the distal end opening 35c; and the helical slit 54 on the proximal end side. According to this configuration, when the cannula 35 is punctured into the body tissue, the insertion resistance received from the body tissue causes the distal end part of the cannula 35 to enlarge its diameter, thus, providing an effect of increasing the amount of sampled body tissue.

[Fifth Modification]

Figure 15:
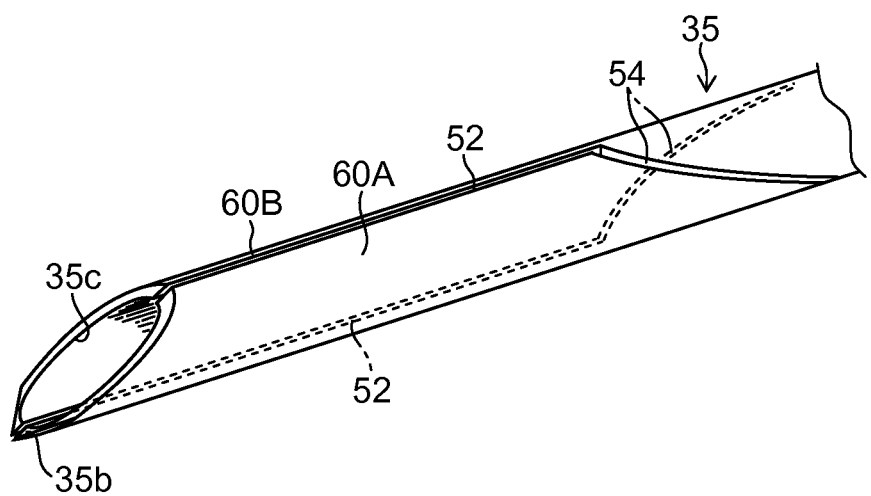
FIG. 15 is a perspective view illustrating a distal end part of the cannula according to a fifth modification.
Figure 16:
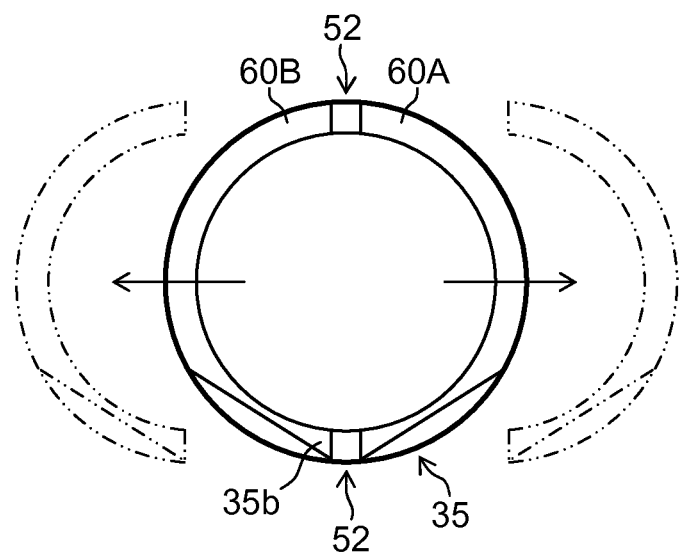
FIG. 16 is a front view illustrating the distal end part of the cannula according to the fifth modification.

The fifth modification illustrated in FIG. 15 is a combination of the present embodiment and the fourth modification. More specifically, the distal end part of the cannula 35 includes two pairs of the distal end side slit 52 and the proximal end side slit 54, and the slits 52 and 54 include elastic pieces 60A and 60B respectively. According to this configuration, as illustrated by the imaginary line in FIG. 16, when the distal end part of the cannula 35 is projected from the distal end of the sheath 34, each of the elastic pieces 60A and 60B enlarges its diameter in a mutually different direction, thus allowing a further larger amount of body tissue to be sampled than the embodiment of providing a single elastic piece 60.

What is claimed is:

1. A tissue sampling device comprising:
a flexible sheath; and
a cannula configured to be inserted into the sheath so as to be movable back and forth and adapted to puncture body tissue, wherein
the cannula has a distal end part including a slit extending from a distal end opening toward a proximal end side, and has edge parts provided on both sides of the slit and including a first edge part and a second edge part,
the cannula is configured such that a first curvature radius of a shape of the first edge part along a plane perpendicular to a longitudinal direction of the cannula is larger than a second curvature radius of a shape of the second edge part along the plane,
a proximal end side of the slit is spirally formed, in the longitudinal direction of the cannula, to be a spiral part of the slit, such that a distal end side of the slit has a uniform width,
the slit is straight between a distal end of the spiral part of the slit and a distal end of the entire slit,
the first edge part is formed in a sharp edge shape, and in the plane perpendicular to the longitudinal direction of the cannula, a needle tip of the cannula is not included in a circumferential range in which the spiral part of the slit is formed.

2. The tissue sampling device according to claim 1, wherein in a state where the distal end part of the cannula is protruded from the distal end of the sheath, the first edge part enlarges a diameter of the cannula to be greater than an inner diameter of the sheath.

3. The tissue sampling device according to claim 1, wherein the distal end part of the cannula is less than or equal to an inner diameter of the sheath when housed in the sheath.

4. The tissue sampling device according to claim 1, wherein the slit extends to the proximal end side from other than a sharpened tip portion of the distal end opening of the cannula.

5. The tissue sampling device according to claim 1, wherein the slit extends to the proximal end side from a sharpened tip portion of the distal end opening of the cannula.

6. The tissue sampling device according to claim 1, wherein an inner surface of the distal end part of the cannula includes a guide member for guiding body tissue trapped inside the distal end part of the cannula to the proximal end side when the cannula is rotated.

7. A tissue sampling device comprising:
a flexible sheath; and
a cannula configured to be inserted into the sheath so as to be movable back and forth and adapted to puncture body tissue, wherein
the cannula has a distal end part including a slit extending from a distal end opening toward a proximal end side,
a first edge part and a second edge part are provided on both sides of the slit,
an elastic piece elastically deformable in a radial direction is provided at the first edge part,
when the cannula is protruded from a distal end of the sheath, the elastic piece is enlarged in diameter radially outward from an inner surface of the sheath along a plane perpendicular to a longitudinal direction of the cannula, so that a first curvature radius of a shape of the first edge part along the plane is larger than a second curvature radius of a shape of the second edge part along the plane,
when the cannula is housed in the distal end of the sheath, the elastic piece is reduced in diameter radially inward from the inner surface of the sheath by the sheath along the plane,
a proximal end side of the slit is spirally formed, in the longitudinal direction of the cannula, to be a spiral part of the slit, such that a distal end side of the slit has a uniform width when the cannula is protruded from the distal end of the sheath,
the slit is straight between a distal end of the spiral part of the slit and a distal end of the entire slit,
the first edge part is formed in a sharp edge shape, and in the plane perpendicular to the longitudinal direction of the cannula, a needle tip of the cannula is not included in a circumferential range in which the spiral part of the slit is formed, so that when the cannula is protruded from the distal end of the sheath and the elastic piece is enlarged, the needle tip is not directly affected by the enlargement of the elastic piece and hence a position of the needle tip is fixed allowing stable puncture and permitting the needle tip unmoved during puncture.

* * * * *